United States Patent [19]
Jeffery

[11] Patent Number: 5,917,881
[45] Date of Patent: Jun. 29, 1999

[54] DIGITAL SCAN MAMMOGRAPHY APPARATUS UTILIZING VELOCITY ADAPTIVE FEEDBACK AND METHOD

[75] Inventor: Gregory R. Jeffery, Lyons, Colo.

[73] Assignee: Fischer Imaging Corporation, Denver, Colo.

[21] Appl. No.: 08/859,491

[22] Filed: May 20, 1997

[51] Int. Cl.[6] .................................................. H05G 1/64
[52] U.S. Cl. ......................................... 378/98.8; 378/146
[58] Field of Search ................................... 378/98.8, 146

[56] References Cited

U.S. PATENT DOCUMENTS

| | | | |
|---|---|---|---|
| Re. 32,164 | 5/1986 | Kruger ...................................... | 378/19 |
| Re. 32,779 | 11/1988 | Kruger ...................................... | 378/19 |
| 4,096,391 | 6/1978 | Barnes ..................................... | 250/505 |
| 4,157,572 | 6/1979 | Kennedy et al. ......................... | 360/33 |
| 4,174,481 | 11/1979 | Liebetruth ............................... | 250/445 |
| 4,179,100 | 12/1979 | Sashin et al. ............................ | 250/416 |
| 4,203,037 | 5/1980 | Gur et al. ................................. | 250/505 |
| 4,247,780 | 1/1981 | Webber et al. .......................... | 250/491 |
| 4,298,800 | 11/1981 | Goldman .............................. | 250/445 T |
| 4,366,574 | 12/1982 | Hill .......................................... | 378/99 |
| 4,383,327 | 5/1983 | Kruger ..................................... | 378/19 |
| 4,692,937 | 9/1987 | Sashin et al. ............................ | 378/62 |
| 4,696,022 | 9/1987 | Sashinet al. ............................. | 378/41 |
| 4,744,099 | 5/1988 | Huttenrauch et al. .................. | 378/157 |
| 4,946,238 | 8/1990 | Sashin et al. ........................ | 350/96.27 |
| 4,998,270 | 3/1991 | Schied et al. ............................ | 378/37 |
| 5,142,557 | 8/1992 | Toker et al. .............................. | 378/37 |
| 5,289,520 | 2/1994 | Pellegrino et al. ...................... | 378/208 |
| 5,335,257 | 8/1994 | Stunberg ................................... | 378/37 |

OTHER PUBLICATIONS

Yaffe, "Digital breast techniques excel at image display", Diagnostic Imaging, May, 1993, pp. 79, 80, 82, 85 and 105.
Jackson et al., "Imaging of the Radiographically Dense Breast", Radiology, Aug. 1993, pp. 297–300.

*Primary Examiner*—Craig E. Church
*Attorney, Agent, or Firm*—Holme, Roberts & Owen LLP

[57] ABSTRACT

An improved imaging system produces consistent, high resolution digital images of a region of interest within a patient's breast by optimizing the modulation transfer function of the system. The system includes an array of detector elements and a source, positioned in opposing relation to the detector element array, for transmitting an imaging signal to the detector array with the region of interest positioned therebetween such that the detector array receives the imaging signal. The array is configured for scanning movement such that imaging data is detected and accumulated within the elements of the array during the movement. The detector array is further configured for reading out a portion of the accumulated data in response to a drive input and for internally shifting the accumulated imaging data in response to a shifting signal. The shifting signal is modified in accordance with measured variations in the scanning rate such that a substantially fixed relationship is maintained between the region of interest and the position of the accumulated charge within the array during the scanning movement, irrespective of variations in the rate of scan.

30 Claims, 6 Drawing Sheets

DIGITAL SCAN MAMMOGRAPHY APPARATUS UTILIZING VELOCITY ADAPTIVE FEEDBACK AND METHOD

FIELD OF THE INVENTION

The present invention relates generally to digital radiology and, in particular, to an apparatus for scanning a receiver across a selected region of a patient's anatomy while receiving an imaging signal which has passed through the selected region. Acquisition and readout of imaging data by the receiver is controlled in response to the rate of movement of the receiver during scanning. The invention has particular application to mammography.

BACKGROUND OF THE INVENTION

In the field of radiology, breast imaging is considered to be one of the most demanding in terms of resolution and contrast. Specialists in the field are interested in imaging lesions or masses that may require an imaging aperture that is about 50 microns in size or less. At the same time, contrast requirements are also demanding since the lesions or masses to be imaged sometimes have x-ray absorption characteristics similar to that of the surrounding tissue. Moreover with heightened interest in early detection, image resolution and contrast demands are continuing to increase.

X-ray mammography has been performed using both film-based and digital systems. In film-based systems, x-rays are transmitted through the patient's breast and impinge upon a phosphor screen. Light emitted from the phosphor screen, due to excitation by the impinging x-rays, is used to expose a light sensitive film. The film is then developed to yield an image of the patient's breast which can be viewed on a light box. In digital systems, a light sensitive receiver is used in place of the film. The receiver yields an electronic signal which can be processed for real-time viewing on a high-resolution monitor.

Improvements in film-based, x-ray imaging systems have resulted in improved image resolution and exposure of the patient to lower radiation dosages. Film-based systems are subject, however, to certain limitations. For example, film granularity and film screen noise limits the spatial resolution of the resulting image. Moreover, films which produce higher resolution images generally require greater radiation doses. Additionally, the resulting image contrast can be significantly affected by scattered radiation. Although the effects of scattered radiation may be reduced by using an anti-scatter grid, the latter necessitates a greater radiation dosage.

Digital systems are advantageous in that the above described problems involving film granularity and film screen noise are avoided while theoretically being capable of providing outstanding image resolution. In addition to high resolution, digital imaging systems provide other advantages including the ability to manipulate various processing and display parameters for an image, once the image has been stored, to optimize its display. Provisions for real-time imaging capability are also advantageous in that procedures such as, for example, biopsies may be performed while viewing a real-time image of the tissue site with biopsy instruments applied thereto.

The ability of a digital system to image, or replicate, a given area may be represented as a modulation transfer function (MTF). The MTF ranges in value from 0 to 1 wherein a value of 1 represents a theoretically perfect image duplication of the area while a value of 0 represents no duplication of the area of interest. Many factors may contribute to deterioration of the MTF in a digital system including, but not limited to, mechanical tolerances, frictional implications of interfacing mechanical components and design/production variabilities in the digital camera being used. Of course, the objective in producing imaging systems is to provide the highest possible MTF in a cost-effective manner.

One recent advance in digital imaging systems utilizes a scanned receiver in a time delay integration (TDI) mode. This technique is described in detail in U.S. Pat. No. 5,526,394, which is assigned to the assignee of the present invention and is incorporated herein in its entirety by reference. In brief, the TDI receiver is scanned across a region of interest during its exposure to a radiation signal. At the same time, drive signals are provided to the receiver such that electrical charge is incrementally accumulated, or integrated, by the receiver and output from the receiver as imaging data. The scanned TDI approach provides significant advantages over prior art systems including, but not limited to, reducing the effects of scattered radiation, providing for full field breast imaging and reducing the required radiation dosage.

SUMMARY OF THE INVENTION

The present invention combines the aforementioned advantages of scanned time delay integration (TDI) with a method and apparatus for synchronizing receiver operation with scanning movement in order to optimize the modulation transfer function (MTF) and thereby provide consistent, high resolution digital images of a region of interest. As such, the invention is particularly apt for mammography applications.

More particularly, a method and associated system are provided for generating an image of a selected region of interest within a patient's breast via scanning with enhanced velocity adaptive image readout. The system includes an array of detector elements implemented for scanning movement, during which movement radiation image data is detected by and incrementally accumulated within the elements of the array. The detector array is configured for reading out successive portions of the accumulated data in response to a drive input. In this regard, the system includes a monitoring arrangement for providing an output in response to the monitored scanning movement of the detector array. Such output is used to provide a shifting signal to the drive input so as to read out the portions of accumulated data in corresponding relation to the scanning movement.

In one aspect of the invention, the system further includes a source, positioned in opposing relation to the detector element array, for transmitting an imaging signal to the detector array with the selected breast region positioned therebetween such that the detector array receives the imaging signal. The detector array includes a shifting arrangement for driving the array elements to shift the incrementally accumulated imaging data within the array and to read out the accumulated imaging data therefrom. The scanning movement is provided by scanning means. In response to the output of the monitoring arrangement, a processor provides the shifting signal to the shifting arrangement to initialize the read out of the portion of accumulated charge for composing a portion of an image as well as to shift the accumulated charge within the detector array.

In accordance with the present invention, the processor is configured for modifying the shifting signal based, at least in part, on the output of the monitoring arrangement such that a substantially fixed relationship is maintained/ coordinated between any given portion of the region being imaged and the position of the corresponding accumulated charge within the array during the scanning movement, irrespective of variations in the rate of scanning movement. In this manner, shifting and readout control of the imaging data is electronically matched with variations in the rate of actual scanning movement to substantially enhance the MTF of the system.

In accordance with this latter aspect, the scanning velocity at which the array is moved by the scanning drive may be permitted to float at a substantially constant rate. In this regard, the scanning drive and overall mechanism disclosed herein is designed to substantially eliminate frictional components and mechanical constraints which may adversely influence a constant scanning rate.

In still another aspect of the present invention, the shifting signal is modified based upon measuring the duration of incremental movements of the detector array wherein each incremental movement corresponds with a shifting interval. In one embodiment, the duration of a first incremental movement, which occurs during a first shifting interval, is measured. Thereafter, the duration of a second or next shifting interval is set to the measured duration of the first incremental movement to match the shifting rate of accumulated data within the array to the measured scanning movement. In another embodiment, shifting signal modification is accomplished by measuring the durations of successive first and second incremental movements corresponding with respective first and second shifting intervals. These movement durations are compared and the duration of a third or next shifting interval is set to the measured duration of the second incremental movement, if a predetermined difference exists between the measured duration of the first and second incremental movements to match the shifting rate to the measured scanning rate. It will be appreciated that any number of alternative methods may be employed to match the shifting signal to the scanning rate in accordance with the teachings of the present invention.

In yet another aspect of the present invention, monitoring of detector array movement is accomplished by moving the detector array in a series of predetermined incremental movements during the scan. The aforementioned output is produced at a plurality of successive positions during each increment such that a change in the signal is substantially directly attributable to a change in the scanning rate. In one embodiment, such monitoring is implemented in a highly advantageous way by using an elongated, holographically produced encoder strip to define the successive positions during each increment. During the scan, an encoder moves in unison with the detector array and relative to the encoder strip while reading the latter to produce an output pulse at each successive position. The pulses are counted to establish the completion of an incremental movement and the overall position of the detector array within a respective scan. The time duration of each increment may be established, as pulse counting is performed, by monitoring elapsed time as measured against a highly accurate crystal controlled clock.

As one advantage of the present invention, the MTF of the system is enhanced by shifting data and reading data out of the detector element array at a rate which is electronically adapted to the measured velocity of the detector array. Therefore, the system is able to accurately and expediently compensate for unavoidable and minute variations in the scanning rate due to, for example, mechanical constraints.

As another advantage, the inventive system permits the scanning drive arrangement to move the detector array at a free floating velocity without the need to employ a conventional electromechanical servo loop. Thus, an "electronic" time constant is used as opposed to a conventional servo loop control avoid imposing a relatively slow electromechanical time constant which may adversely degrade the system MTF.

Although the present invention is specifically described herein with respect to breast imaging applications, it will be appreciated that various aspects of the present invention can be utilized in connection with imaging other body regions.

BRIEF DESCRIPTION OF THE DRAWINGS

For a more complete understanding of the present invention and further advantages thereof, reference is now made to the following Detailed Description, taken in conjunction with the Drawings, in which.

DETAILED DESCRIPTION OF THE INVENTION

Figure 1:
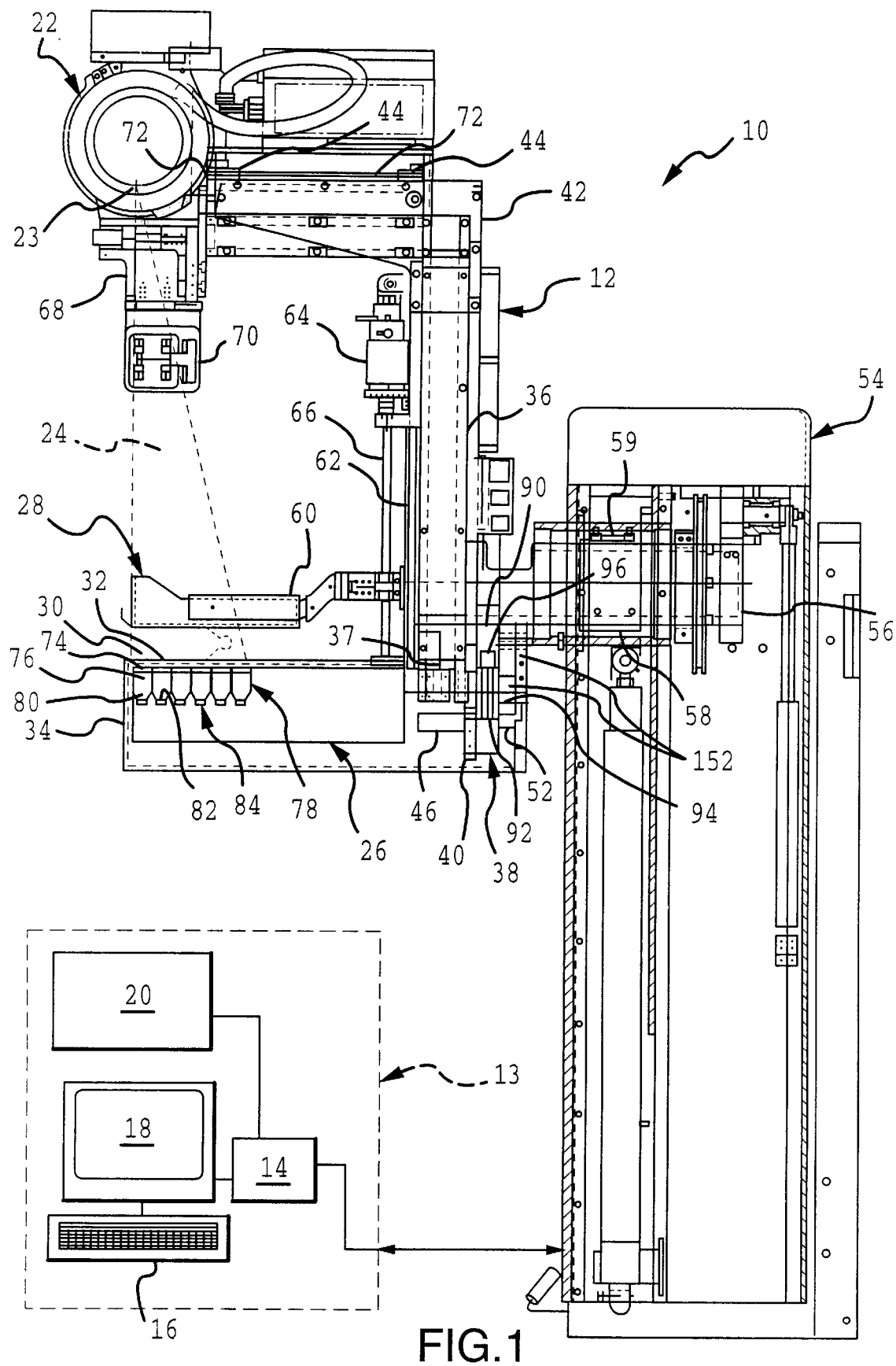
FIG. 1 is a diagrammatic cross-sectional view, in elevation, generally illustrating a digital imaging station and monitoring terminal manufactured in accordance with the present invention.

FIG. 1 illustrates a digital imaging system 10 manufactured in accordance with the present invention. System 10 includes a digital scanning station 12 and a monitoring station 13. Monitoring station 13 includes a processor 14 connected with a user interface 16 which may comprise, for example, a keyboard. A display 18, which is generally a CRT type display device, and a high-resolution image printer 20, for printing diagnostic quality images, are also provided. While system 10 is configured for the application of mammography, it should be understood that the teachings of the present invention are adaptable to a variety of other imaging applications.

Continuing to refer to FIG. 1, processor 14 may comprise a number of different processing subsystems (not shown), each of which may include one or more central processing units which are dedicated to performing certain tasks associated with the operation of system 10. In this regard, it is to be understood that a wide array of hardware architectures may be adaptable for use in practicing the present invention.

Components of scanning station 12 include an imaging signal source 22 such as, for example, an x-ray tube for producing a focused imaging signal 24, an imaging signal receiver 26 such as a digital camera, a compression assembly 28 for compressing and immobilizing a patient's breast 30 against an upper surface 32 of a receiver housing 34, and a pendulum assembly 36. Pendulum 36 includes a lower end 37 which supports receiver 26 and a scanning drive assembly 38 on a bracket 40. An upper end 42 of pendulum 36 is pivotally supported by bearings 44 so as to provide for movement of receiver 26 in a direction which is generally parallel with the patient's chest wall. Scanning movement is provided by a micro-stepper motor 46 which is mounted on bracket 40 for scanning receiver 26 across a particular region of interest within the patient's breast.

In accordance with the present invention, the scanning velocity of receiver 26 is allowed to float and is not monitored within a feedback loop. Further details regarding this arrangement will become evident with the continuing description of the present invention. For the moment, it is important to note that micro-stepper motor 46 should be capable of providing significant angular torque so as to maintain a substantially constant scanning velocity in the present application when a constant drive signal is applied thereto. One such micro-stepper motor is the Vexta series 5 phase which is available from Oriental Motor. However, other micro-steppers may also be found to be useful. Scanning movement is detected by an encoder 52, also mounted on bracket 40. Details of the arrangements of micro-stepper motor 44 and encoder 52 will be provided at appropriate points below.

Still referring to FIG. 1, imaging signal source 22, receiver 26, compression assembly 28, scanning drive assembly 38 and related components are carried by and rotatably mounted on a pedestal 54 via a shaft 56 which is received by bearings 58 such that images may be obtained at various imaging angles as these components are rotated about shaft 56 and the patient's breast in a direction generally parallel with the patient's chest wall. Once a desired position is attained, these components can be locked into position by a brake assembly 59.

Compression assembly 28 includes a compression paddle 60 which rides along rails 62. A compression motor 64 drives a threaded output shaft 66 which threadably engages paddle 60. Thus, the latter may be moved downward, in the depicted orientation, so as to compressively engage and thereby immobilize the patient's breast, while providing a more uniform tissue thickness for imaging.

Imaging is accomplished by scanning imaging signal 24 across the patient's breast. As illustrated, imaging signal 24 originates from signal source 22 and passes through a filtering assembly 68 and collimator assembly 70. Consequently, the imaging signal 24 incident upon the patient's breast comprises a narrow, fan-shaped x-ray beam with characteristics suited to the thickness, density or other attributes of the tissue being imaged. Signal source 22 is mounted on a shaft 72 which is rotatably received by bearings 44 and interconnected to upper end 42 of pendulum assembly 36 so as to rotate with pendulum 36 during scanning movement. More particularly, a focal point 23 of source 22 is aligned coaxially with shaft 72 such that scanning movement of receiver 26 co-drives synchronous movement of source 22. As may be seen in FIG. 1, imaging signal 24 is of sufficient width to provide for full field imaging of the patient's breast. Since paddle 60 and upper surface 32 of receiver housing 34 are formed from materials which are transparent to the imaging beam, the beam is incident on receiver 26 after passing through the patient's breast tissue.

Receiver 26 comprises a digital camera including a row of phosphorescent screens 74 which are configured to generally match signal 24 in cross-section. Screens 74 produce light responsive to imaging signal 24 which light is coupled to a pickup end 76 of a respective one of a plurality of image reducing fiber optic tapers 78. Light received by pickup end 76 is transferred to an emitting end 80 of each taper. Emitting end 80 of each taper is, in turn, coupled to a light sensitive upper surface 82 of a CCD chip 84. In the present example six CCDs are utilized, however, one of skill in the art will recognize that the teachings of the present invention are applicable to any number of CCDs.

Figure 2:
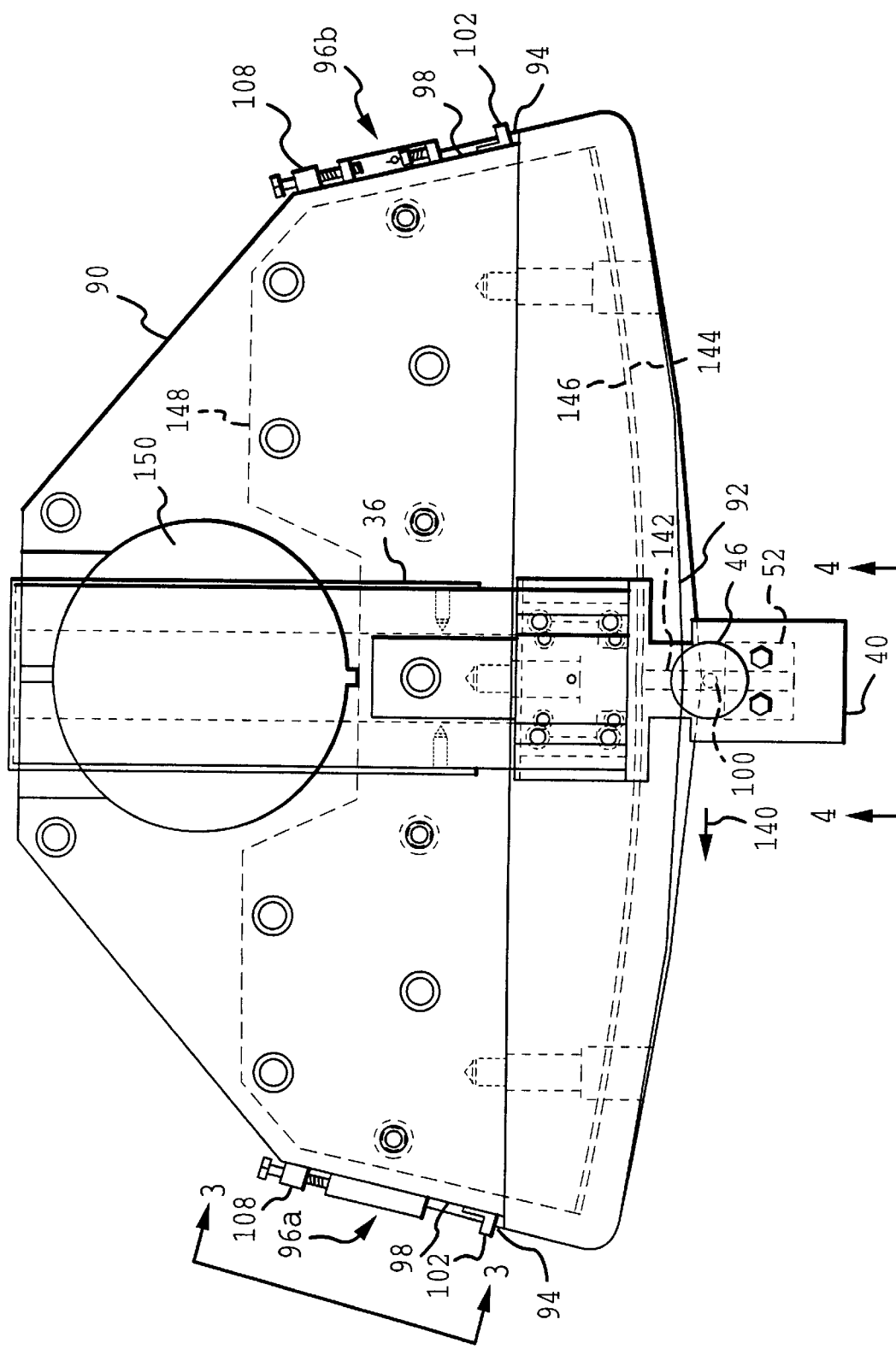
FIG. 2 is a diagrammatic, enlarged end view, in elevation, illustrating the arrangement of a cam assembly within the overall configuration of the imaging station of FIG. 1, shown here to illustrate details of its construction.
Figure 3:
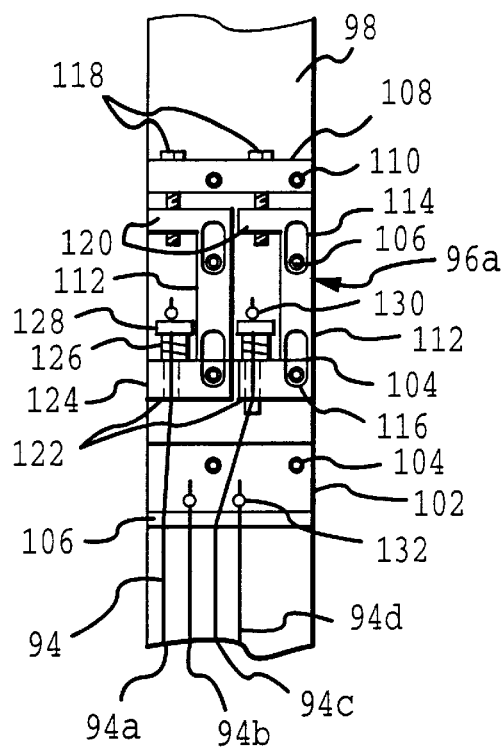
FIG. 3 is a view taken generally from line 3—3 of FIG. 2 illustrating details of the construction of a cable tensioning assembly manufactured in accordance with the present invention.

Details relating to scanning drive arrangement 38 are generally illustrated in FIG. 1 with specific details being shown in FIGS. 2 and 3, wherein FIG. 2 provides an enlarged end view of a drive cam 90 defining a lower arcuate surface 92. A plurality of flexible cables 94 extend between a pair of tensioning arrangements 96a and 96b which are mounted on opposing side margins 98 of drive cam 90 such that the cables are supported by arcuate surface 92 of drive cam 90. In the present embodiment, four cables 94a–d are used each of which includes a diameter of approximately 0.024 of an inch and is formed from stranded stainless steel. It should be appreciated that different numbers of cables may be used in accordance within the present invention. Moreover, cables including other diameters and materials may be found to be useful provided that they are sufficiently strong, flexible and resistant to elongation under prolonged tension. Each tensioning arrangement 96 includes a spacer block 102 which is fixedly attached to side margin 98 using a pair of fasteners 104. Each of cables 94a–d are slidably received in a slot 106 on the spacer block so as to space the cables laterally equidistant from one another.

Referring to FIG. 3, the components of tensioning assembly 96a will be described. Tensioning assembly 96b is identical with assembly 96a except as noted below. Tensioning assembly 96a further includes an adjustment block 108, which is fixedly mounted to side margin 98 using fasteners 110, and two C-shaped members 112 defining elongated slots 114. A plurality of fasteners 116 are positioned in elongated slots 114 to slidably retain C-shaped members 112 against side margin 98 of drive cam 90 thereby permitting the C-shaped members to move vertically along the side margin. Threaded bolts 118 threadably engage an upper arm 120 of each C-shaped member and are slidably received in adjustment block 108 such that the heads of bolts 118 are supported against adjustment block 108. Cables 94a and 94c each pass through an opening 122 defined by a lower arm 124 of each C-shaped member. Cables 94a and 94c then travel along the axis of helical springs 126 and through associated end caps 128 which are positioned over the upper ends of the springs. These cables are then fitted with end stops 130 which may be of the crimp on type. Cables 94b and 94d do not extend to the C-shaped members, but are retained against spacer block 102 at slots 106 by still more end stops 132. In tensioning assembly 96b, the cables are oppositely arranged (not shown). That is, cables 94a and 94c are terminated by end stops 132 immediately adjacent slots 106 while cables 94b and 94d are received by the lower arms of the C-shaped members.

To apply tension to cables 94, bolts 118 are adjusted so as to move C-shaped members 112 upward, away from their associated spacer block 108 such that end cap 128 is forced against stop 130 by spring 126 on the respective cables. Continued movement compresses spring 126 between lower arm 124 of the C-shaped member and end cap 128 so as to resiliently tension each cable. In the present example, tensioning arrangements 96 are configured to place approximately 14 pounds of tension measured at the center of the cables. The features of the tensioning arrangement as taught herein are particularly advantageous, as will be described below. Furthermore, it should be appreciated that one of ordinary skill in the art may devise many alternative tensioning assemblies in the application of the teachings of the present invention.

Figure 4:
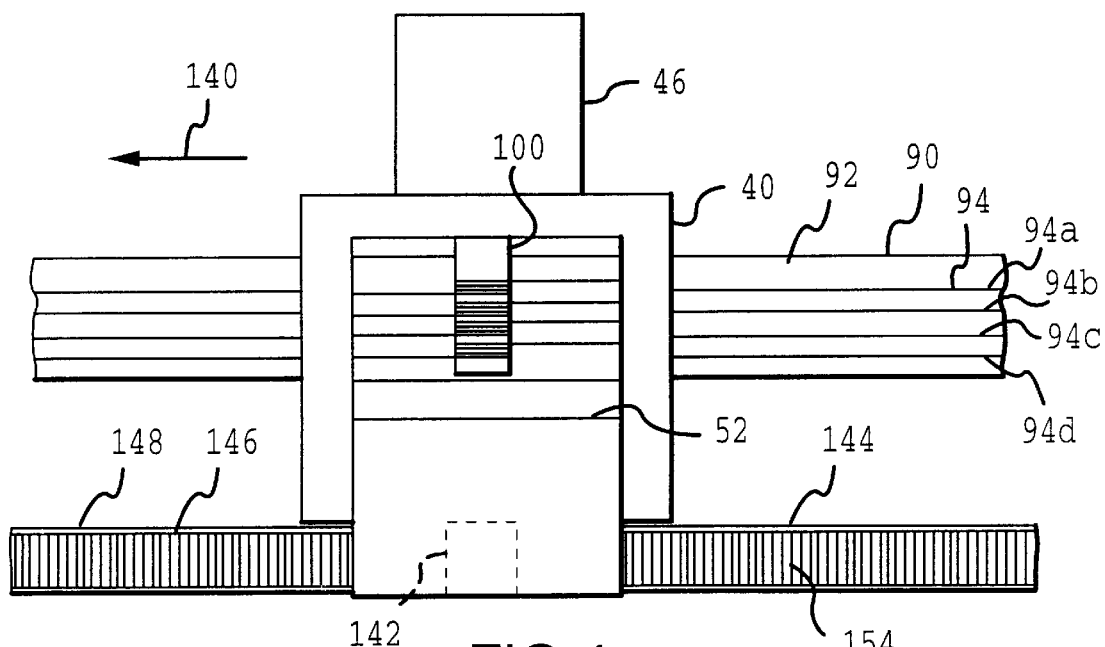
FIG. 4 is a view taken generally along line 4—4 of FIG. 2 diagrammatically illustrating a scanning drive and monitoring assembly used to scan a digital camera and to provide accurate information as to the position and movement of the camera.

Turning now to FIGS. 2 and 4, micro-stepper motor 46 includes a bi-directional output shaft 100 which engages cables 94. Normally cables 94 remain tensioned against arcuate surface 92 by tensioning assemblies 96. However, in the immediate area of micro-stepper motor shaft 100, cables 94 are lifted from the drive cam due to their each being wrapped around output shaft 100. In the present embodiment, each cable encircles the output shaft a total of four times. Precision of the scanning movement may be controlled by the step resolution of micro-stepper motor 46. In the present example, an incremental rotation of 0.328 degrees of the motor shaft provides for an incremental movement in a scanning direction, indicated by an arrow 140, of approximately 60$\mu$. It should be mentioned that various factors influence the relationship between incremental rotation of the motor shaft and movement in the scanning direction, such factors include the diameter of the motor shaft and the distance of the motor from the pivoting point (bearings 44, FIG. 1) of pendulum 36.

It should be appreciated that features embodied in the mechanics of the scanning drive configuration described immediately above provide for smooth scanning motion of pendulum 36 throughout the duration of a scan while maintaining precise positional control. These features are particularly advantageous in view of the technique employed herein where micro-stepper motor 46 is operated at a fixed rate with the objective of realizing a floating, yet substantially constant scanning rate. As one example, because micro-stepper motor 46 is capable of exerting considerable angular torque, forces applied to cables 94 by the micro-stepper may be significant. This concern is addressed by one feature of tensioning assemblies 96 with regard to the arrangement of cables 94. More specifically, in either direction of advancement by the micro-stepper, alternating ones of cables 94 have end stops 132 which transfer the micro-stepper forces directly to spacer blocks 102. This feature avoids positional errors derived from compressing springs 126 in the tensioning assemblies. As another example, the scanning drive arrangement is configured to avoid slipping of output shaft 100 of the micro-stepper with respect to cables 94. Features contributing to avoid slippage include proper application of tension to the cables by the tensioning assemblies and the number of wraps (four) of each cable around output shaft 100. Moreover, frictional components in the overall mechanism should be eliminated to the extent possible in order to realize as smooth a scanning motion as is mechanically achievable.

Continuing to refer to FIGS. 2 and 4, the arrangement of encoder 52 within system 10 will now be described. As previously mentioned, encoder 52 is mounted on bracket 40 which is, in turn, mounted on the lowermost end of pendulum 36. Encoder 52 includes a read head 142 which reads an encoder strip 144. The latter is mounted on an arcuate encoder surface 146 of an encoder cam 148. It is noted that in the view of FIG. 2, encoder cam 148 and encoder strip 144 are positioned behind drive cam 90 while encoder 52 is positioned behind bracket 40 on pendulum 36. Therefore, all these components are illustrated using dashed lines. In fact, encoder cam 148 may be used to support drive cam 90. In the present example, drive cam 90 is supported by shaft 56 (FIG. 1) which extends through opening 150 in cam 90 and by encoder cam 148 using an intermediate spacer 152 (FIG. 1) so as to be rotatably carried by shaft 56. Encoder strip 144 includes a series of marks 154 which are precisely positioned on the strip. In the present example, encoder strip 144 is produced using holographic techniques such that marks 154 are separated by a distance of 1 micron within an error of ±0.15$\mu$. It should be mentioned that the resolution of marks 154 in the accompanying figures is greatly enlarged for purposes of illustration. In fact, the actual resolution of these marks is so fine that they are not individually distinguishable by the unaided eye.

During an imaging scan driven by micro-stepper motor 46, pendulum 36 moves encoder 52, along with receiver 26, in the direction of arrow 140. As the encoder read head 142 views encoder strip 144, it produces an electrical signal such as, for example, a pulse in response to each passing mark 154. Like encoder strip 142, encoder 52 is highly accurate, producing its output pulses in precise correspondence with the reading of each mark 154 through the use of infrared diodes. Therefore, it should be appreciated that the precision of marks 154 coupled with encoder 52 provides for correspondingly precise tracking and/or monitoring of scanning velocity and the position of the pendulum relative to the region being imaged to within an approximate overall error of ±0.5%. This tracking process is carried forth in a highly advantageous way which has not been seen heretofore and which will be described below in conjunction with a discussion of the method of the present invention.

Figure 5:
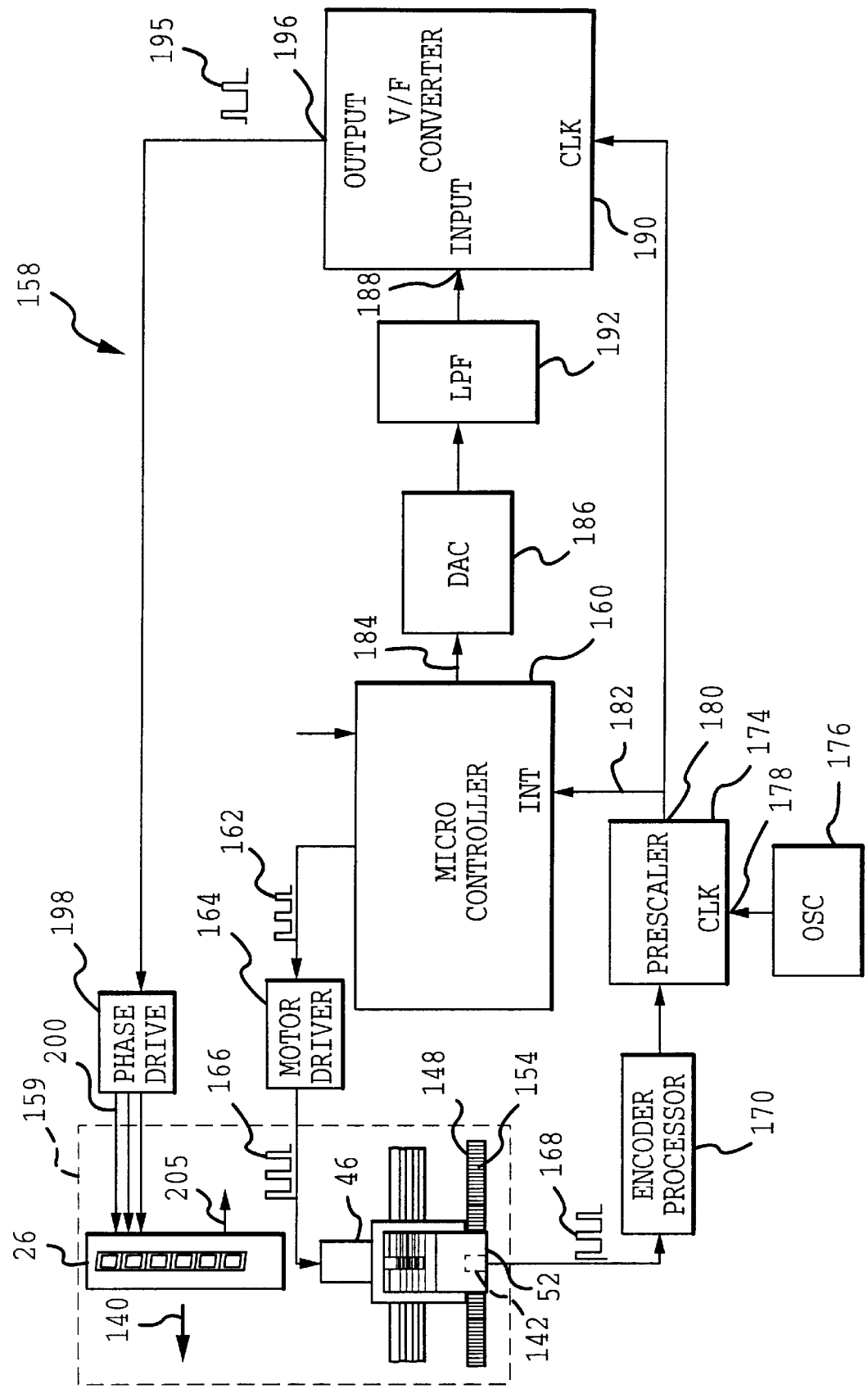
FIG. 5 is a block diagram illustrating one embodiment of a scanning drive circuit in relation to components illustrated in FIGS. 1–4.

Having generally described the components which make up system 10, attention is now directed to FIG. 5 which illustrates a scanning drive circuit 158 in block diagram form in electrical communication with components (enclosed within a dashed line 159) positioned on the lower end of pendulum 36 (FIG. 1). These components include receiver 26, micro-stepper motor 46 and encoder 52. While the following discussion describes one implementation of circuitry 158 using specific, commercially available parts, it is to be understood that circuitry 158 may be implemented in an unlimited number of ways in accordance with the present invention. In the present embodiment, scanning drive circuitry 158 includes a motion control section 160 which provides a series of motor drive pulses 162 to a motor driver section 164 during an imaging scan in the direction of arrow 140. It should be noted that pulses 162 are not varied in frequency during the scan by any form of feedback circuitry, but rather are generated at a fixed frequency, f1 such that the scanning velocity is allowed to float, as noted previously. Frequency f1 is of a predetermined value which permits the modulation transfer function (MTF) of system 10 to be optimized during scanning. Various factors are considered in determining f1 including, but not limited to, achieving a substantially constant scanning velocity in view of mechanical considerations, optimizing signal to noise ratios of imaging data acquired by camera 26 and speed considerations regarding throughput of the imaging data.

Continuing with a description of FIG. 5, motor drive pulses 166 are then provided to micro-stepper motor 46 from motor drive section 164 so as to cause shaft 100 of the motor to rotate at a substantially constant angular rate, as determined by f1, which progressively takes up cables 94 in the direction of arrow 140. In being generated by motion control section 160, frequency f1 is quite stable since it is derived from a crystal oscillator (not shown) which generates the clock signal for the microcontroller. As one alternative embodiment (not shown), motor drive section 164 may itself be configured to generate pulses 166 at frequency f1 using a separate crystal controlled oscillator. In this case, an on/off input is required from microcontroller 160 or from processor 14 (FIG. 1) to initiate scanning motion. The drive arrangement of cables 94 in conjunction with the high output torque of the micro-stepper motor cooperate to maintain a substantially constant scanning velocity as cables 94 are progressively taken up ahead of and paid out behind motor shaft 100. However, it will be appreciated that small variations in the scanning velocity may occur even though motor 46 is driven at a substantially constant rate. Such variations may be attributed to mechanical tolerances and/or any remaining pre-existing or developing frictional components at certain positions of pendulum 36 during the scan. As an example, friction may occur at a particular position due to binding of bearings 44 (FIG. 1) resulting from an excessive number of operational cycles. Once this friction reaches a significant level, the scanning velocity of receiver 26 will tend to decrease at that position. In a conventional servo control system (not shown), one might expect micro-stepper 46 to form part of a servo control loop as a method of compensating for velocity variations caused by such friction.

A conventional servo arrangement for controlling the velocity of a motor generates an error signal which is proportional to a difference between a desired speed and the actual speed of the motor. Using this error signal, a drive signal to the motor is either increased or decreased so as to bring the motor to the desired speed. As will be appreciated, the time constant in changing the motor speed is relatively slow since the speed of the motor cannot be changed instantaneously due, at least in part, to factors such as overcoming the inertia of the rotating parts of the motor. In the time delay integration technique (TDI), described previously, the MTF of the imaging system is directly related to the speed and degree of precision with which the system can respond to even minute variations in scanning velocity. As will be seen hereinafter, the present invention provides a highly advantageous approach which eliminates the conventional servo control time constant and is capable of improving the MTF of the imaging system to a level which has not been seen previously.

With continuing reference to FIG. 5, read head 142 of encoder 52 "looks at" marks 154 on encoder strip 148 producing a series of encoder pulses 168 in response to the marks. Encoder processor section 170 performs functions such as amplification of pulses 168 and then provides the amplified pulses to a prescaler 174 which is connected with a conventionally configured crystal controlled precision oscillator 176. The latter provides a highly stable clock signal at a clock terminal 178 of the prescaler. In the present example, a clock frequency of 16 MHz is utilized, however, this frequency may be changed provided only that stability is maintained. Prescaler 174 is capable of converting the input frequency of the amplified encoder pulses to a lower frequency which is available at its output terminal 180 by a factor of 16. This functionality facilitates a choice among available cameras, which may operate at different frequencies, since signals generated by the prescaler are ultimately used in driving these different cameras. In the present application, the commercially available GAL22V10 is utilized as prescaler 174. The prescaler passes the amplified and possibly frequency converted encoder pulses directly to a microcontroller 160 on an interrupt line 182 and to other parts of the circuit, as will be described at appropriate points below. One commercially available microcontroller which is suitable for use in the present application is the 80C522 part that is available from Phillips, however, many other parts may also be found to be useful.

Microcontroller 160 outputs two bytes of digital data on parallel data bus 184 (illustrated as a single line for purposes of simplicity) to a sixteen bit Digital to Analog Converter (DAC) 186. DAC 186 then generates an analog control voltage which is coupled to an analog input 188 of a voltage to frequency (V/F) converter 190 via a low pass filter 192. The latter serves to provide protection against potentially injected noise and any Most Significant Byte (MSB) transition spikes from the DAC converter. V/F 190 also receives the scaled encoder pulses from prescaler 174 at a clock input 194. Essentially, the scaled encoder pulses from prescaler 174 set a center frequency for the V/F. The V/F then "pulls" this center frequency based on the analog control signal from DAC 186. Thus, the V/F provides TDI camera drive pulses 195 at an output terminal 196 for use in operating camera 26, as will be described below. The TDI pulses 195 are received by a phase drive circuit 198 which then provides properly phased shifting signals directly to camera 26 on a plurality of phase drive lines 200. In the present embodiment, the commercially available AD652KP, which comprises a crystal controlled, laser trimmed frequency source, is used as V/F 190. It should be mentioned that the AD652KP is an analog configured chip since, in many cases, digital V/F's have undefined outputs during frequency changes. An undefined output from the V/F would result in an MTF of near zero (no image replication) in the present application.

Figure 6:
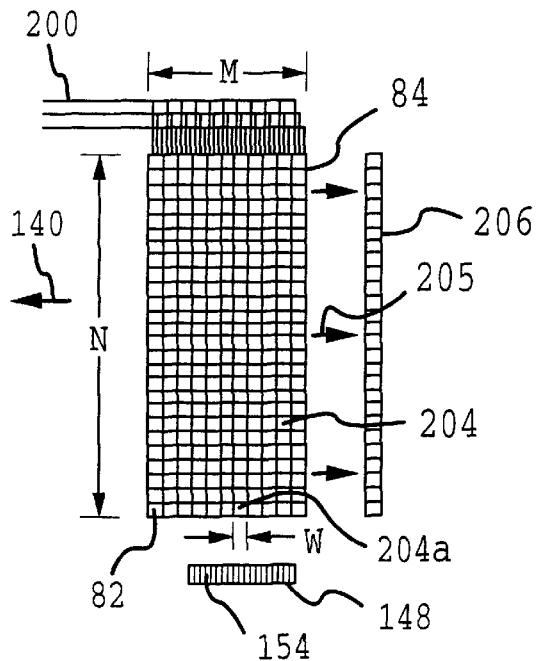
FIG. 6 is a diagrammatic representation of a CCD imaging chip in relation to an encoder strip, both of which are used in the imaging station of FIG. 1.

Turning now to FIG. 6 in conjunction with FIG. 5, a brief discussion will be provided with regard to the operation of camera 26 in the TDI mode. FIG. 6 diagrammatically illustrates a light sensitive surface 82 of one of CCDs 84 used in camera 26 electrically connected with phase drive lines 200. As the phase drive lines are energized with shifting signals generated by phase drive circuit 198, shifting electrodes (not shown) on the CCD are connected with the phase drive lines and energized thereby. The configuration of the CCD in conjunction with the application of potentials via the shifting electrodes, defines an array of potential wells 204 in CCD 84 which are arranged in M lines by N rows. Light emitted from an associated one of phosphorescent screens 74 (FIG. 1) is incident directly upon light sensitive surface 82 and results in the accumulation of electrical charge in potential wells 204 in direct correspondence with the intensity of the incident light.

During an imaging scan, the electrical charge is incrementally shifted across the array of potential wells during a series of shifting intervals in a direction indicated by arrow 205 through proper application of shifting signals to the shifting electrodes such that lines of accumulated electrical charge are individually shifted into a shift register 206. It is mentioned for purposes of clarity that the term "shifting increment", as used in the specification and appended claims, refers to the physical movement of receiver 26 relative to the region being imaged and is not to be confused with the term "shifting interval" which refers to the period of time during which the accumulated electrical charge is shifted by one line within potential well array 204, as determined by the shifting signals applied to phase drive lines 200. One may better appreciate the speed with system 10 operates by noting that the duration of each shifting interval is approximately 1 ms. The accumulated electrical charge for a particular line is then serially read out of shift register 206 and stored as incremental imaging data. By correlating positional information regarding receiver 26 with the incremental imaging data as it is read out, a composite image of the region of interest within the patient's breast may be constructed. However, during the scanning movement, a substantially unvarying relationship should be maintained between the accumulated electrical charge resident in potential wells 204 and the region of interest. To the extent that this relationship is not maintained, the MTF of the imaging system and, consequently, the image generated thereby is degraded. As will be seen hereinafter, the present invention provides a highly advantageous method for maintaining this unvarying relationship between the accumulated charge and the region of interest within the patient's breast.

Figure 7:
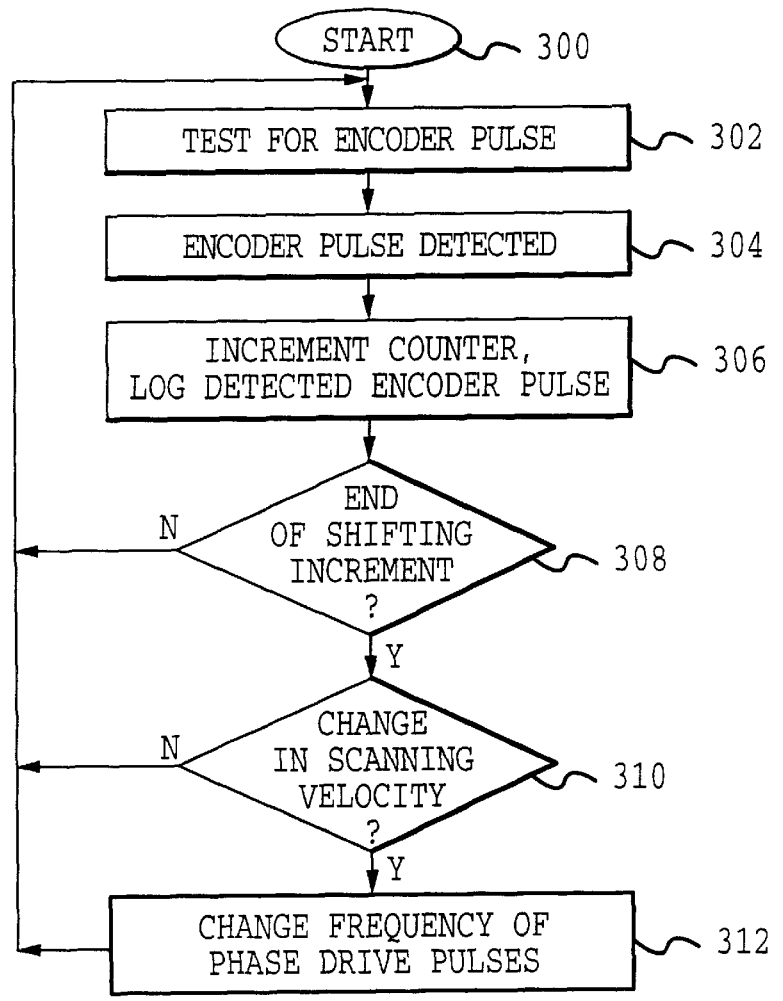
FIG. 7 is a flow chart describing and showing the method of the present invention.

Having generally described the components which make up system 10, the method of the present invention will now be described with reference to the flow diagram of FIG. 7 and with continuing reference to FIGS. 5 and 6. The method begins at start step 300 where a scan begins. At steps 302 and 304, microcontroller 160 monitors interrupt line 182 for the presence of a prescaled encoder pulse from prescaler 174. Once a pulse is detected, step 306 increments an internal counter which logs the exact time at which the pulse occurred and tracks the number of pulses which have been received for the current shifting increment. Additionally, the exact position of receiver 26 in relation to pendulum 36 may be tracked, for example, by using a second counter which accumulates the total number of encoder pulses throughout the scan. As may be seen in FIG. 6, where encoder strip 144 is illustrated immediately adjacent CCD 84, a plurality of encoder pulses are generated for a width w of a particular potential well 204a. As noted previously, the resolution of marks 154 on the encoder strip are so fine that they are not discernible to the naked eye. In the embodiment of FIG. 1, sixty encoder pulses are generated per each shifting increment. Moreover, each mark provides highly accurate positional information regarding the scanning motion of the receiver. Therefore, the rate at which encoder pulses are received is directly indicative of the velocity of the receiver within an extremely small margin of error. In the embodiment of FIG. 1, this error is within the range of 0.5%.

Step 308 checks the number of pulses counted in step 306 for the current shifting increment so as to determine if the current increment has been completed. If not, pulse monitoring continues at step 302. If the current increment has been completed, step 310 is then entered in which the velocity of the receiver, as evidenced by the measured duration of the just completed increment, is monitored. In accordance with the present invention, step 302 measures a first duration of the just completed increment and compares this first duration with a second duration, previously measured, for the increment which immediately preceded the just completed increment. If no difference is detected (i.e. substantially no difference within predetermined system tolerances), between the first and second durations, the value of the control voltage output by DAC 186 is maintained at its current value by microcontroller 160 such that the frequency of camera drive pulses provided by V/F 190 to phase drive circuit 198 are also unchanged in frequency. Monitoring of the next increment then begins at step 302. Alternatively, when the durations of the first and second increments are determined to be of different lengths (i.e. their difference exceeds a predetermined tolerance value) step 312 is next performed.

In step 312, microcontroller 160 determines the percentage difference between the first and second durations, computes a new value for the control voltage based on the percentage difference and sends the new value in digital form to DAC 186 on data bus 184. V/F 190 then pulls i.e., changes the frequency of camera drive pulses provided from its output terminal 196 in accordance with the new value of the control voltage on its input terminal 188. In this manner, the duration of the next shifting interval is effectively adjusted to match the expected duration of its corresponding shifting increment. For example, if the second duration is determined as being five percent shorter than the first duration, i.e., the scanning rate has increased, microcontroller 160 adjusts the control voltage such that the camera drive pulses are generated by V/F 190 at a five percent higher frequency so that the increased velocity of the receiver during the scan is matched by increasing the shifting rate at which accumulated electrical charge is shifted across and read out from potential well array 204 (FIG. 6) in the direction indicated by arrow 205. Similarly, if the second duration is determined as being five percent longer than the first duration, microcontroller 160 adjusts the control voltage such that the camera drive pulses are generated by V/F 190 at a five percent lower frequency to realize a matching five percent decrease in the velocity at which accumulated electrical charge is shifted across and read out from potential well array 204.

In setting the frequency of the shifting signals, the present invention also contemplates the use of microcontroller 160 to store a velocity profile for the system based on the unique scanning characteristics of each individual system. For example, the shifting rate may be set based upon the expected scanning velocity as predicted by the velocity profile. However, direct monitoring of the scanning rate for variations from the predicted rate may occur continuously. In the event that a variation occurs, the shifting rate may be modified accordingly.

In the method described above, it should be appreciated that by allowing the velocity at which receiver 26 is moved during the scan to float while electronically correcting for minute deviations in the velocity, a highly advantageous scanning system is implemented in which the accumulated electrical charge in CCDs 84 is synchronously shifted, based on precise monitoring of the receiver movement, such that a substantially fixed relationship is maintained between the accumulated charge and the area of the patient which is being imaged. The present invention recognizes that the employment of traditional servo loop control for synchronizing scanning motion of the receiver during charge shifting invokes a physically derived time constant which necessarily limits the response time and, as a consequence, the MTF of the imaging system. Therefore, the present invention eliminates traditional electromechanical servo loop control and provides in its place a highly effective method for electronically adapting the charge shifting rate to the scanning movement of the receiver wherein a very fast response time on the order of 250 μs is achieved. Moreover, the method of the present invention relies on highly accurate monitoring of the position of the receiver as provided by the apparatus disclosed herein.

Figure 8:
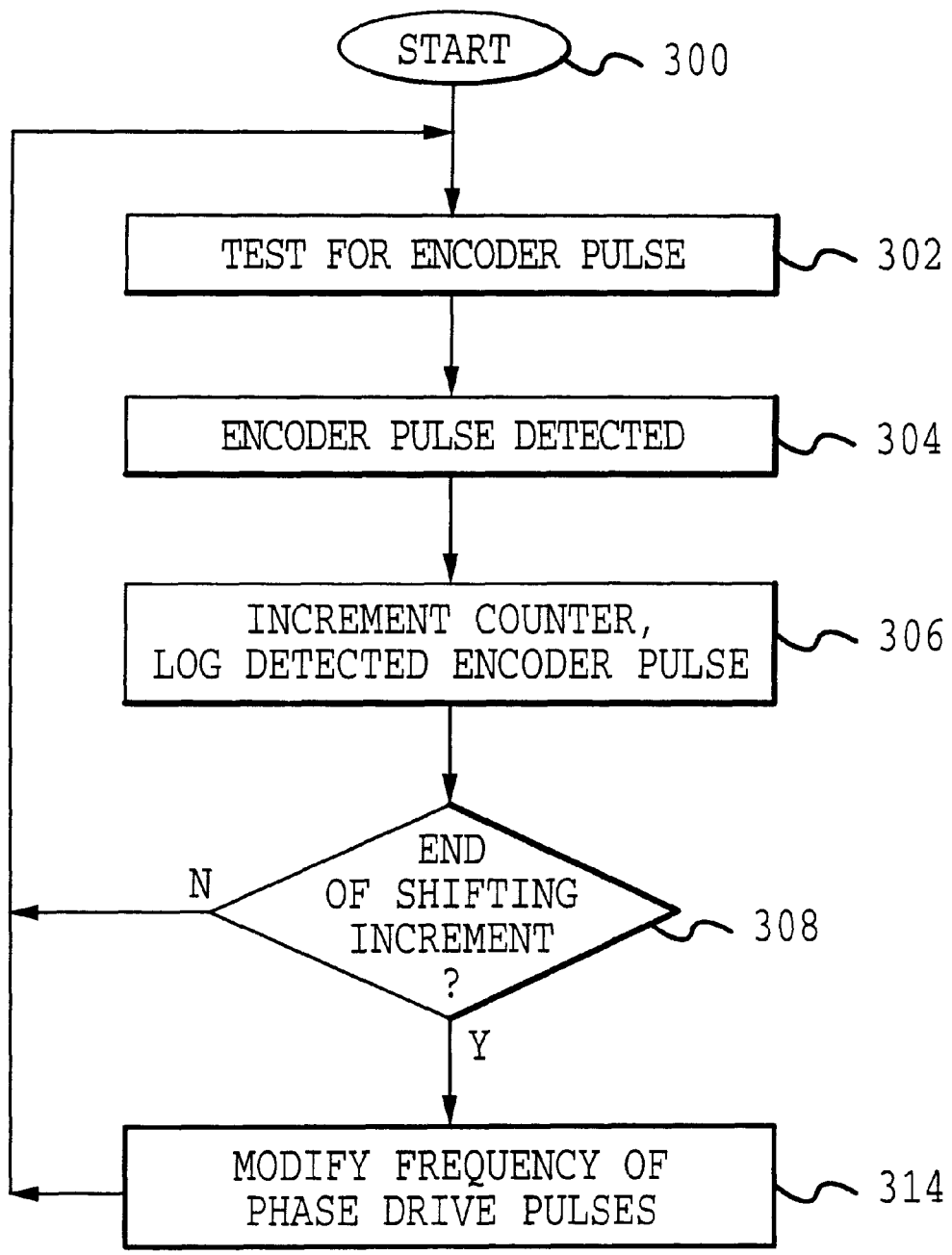
FIG. 8 is an alternative flow chart describing and showing one possible modification of the method of the present invention.

One skilled in the art may devise many alternative configurations for the systems and methods disclosed herein. For instance, the method of the present invention is readily modified in accordance with the flow chart of FIG. 8. In this figure, steps 300 through 308 are unchanged with step 314 being performed following step 308. At step 314, unlike the method of FIG. 7, microcontroller 182 computes a new value for the control voltage based solely on the measured duration of the just completed increment, In other words, the new control voltage adjusts the duration of the next shifting interval, via DAC 184 and V/F converter 190, to coincide with the measured duration of the just completed increment thereby maintaining synchronous shifting of the accumulated electrical charge as the scan proceeds. Therefore, it should be understood that the present invention may be embodied in many other specific forms without departing from the spirit or scope of the invention and that the present examples and methods are to be considered as illustrative and not restrictive, and the invention is not to be limited to the details given herein, but may be modified within the scope of the appended claims.

What is claimed is:

1. A method of imaging a selected region of a patient's body by scanning an array of detector elements, said detector array being configured for movement, during which movement data is detected and accumulated within said array, said detector array further being configured for at least one of shifting and reading out said accumulated data during each of a plurality of shifting intervals in response to a drive input, said method comprising the steps of:

transmitting a radiation beam through the selected region;

moving said detector array;

generating said drive input;

utilizing said drive input for at least one of shifting and reading out said accumulated data during each of a plurality of shifting intervals;

monitoring said detector array movement so as to produce an output, said output being responsive to velocity variations in said detector array movement; and using said output during said generating step to vary said drive input in response to said velocity variations, wherein durations corresponding with said shifting intervals are varied in response to said velocity variations.

2. The method according to claim 1, said utilizing step comprising the step of:

shifting a portion of the accumulated data within said detector array during each of said plurality of shifting intervals as another portion of accumulated data is read out in response to said drive input.

3. The method according to claim 2, said generating step comprising the steps of:

providing shifting pulses at a predetermined shifting frequency which sets an approximate duration for said plurality of shifting intervals; and modifying said predetermined shifting frequency to an actual shifting frequency based on said output to set an actual duration of each said shifting interval.

4. The method according to claim 2 wherein:

said detector array comprises an imaging device for imaging a selected region of a patient's body and for accumulating said data as incremental imaging data within said detector array and said step for shifting the accumulated data includes the step of maintaining a fixed positional relationship between the accumulated data and said selected region during said movement.

5. The method according to claim 2 wherein:

said step for moving the detector array includes the step of moving the detector array along a scanning path in a plurality of predetermined increments; and said step for monitoring said movement includes the steps of (i) measuring a first time duration of a first one of said increments, which occurs simultaneously with a first shifting interval, and (ii) outputting said first time duration as said output.

6. The method according to claim 5, said drive generating step further comprising the step of:

setting a second shifting interval, which immediately follows said first shifting interval and which occurs during a second one of said increments, to a duration corresponding to the measured duration of the first increment.

7. The method according to claim 5 wherein:

said step for monitoring said movement further includes the step of measuring and outputting a second time duration of a second one of said shifting increments; and said drive generating step further includes the steps of (i) comparing the first time duration with the second time duration and (ii) setting a third shifting interval, to be executed next, to a third time duration which is equal to said second time duration provided that the first time duration is of a different length than the second time duration.

8. The method according to claim 5, said monitoring step further comprising the steps of:

(i) producing a series of pulses at predetermined positions along said scanning path such that a predetermined number of pulses are produced per each said increment, (ii) counting said predetermined number of said pulses during said movement, and (iii) measuring said first time duration as a period during which said predetermined number of pulses are counted.

9. A method of generating a composite image of a selected region of a patient's body, said method comprising the steps of:

transmitting a radiation beam from a source means through said selected region of said patient's body;

providing receiving means, disposed in opposing relation to said source means with said selected region of said patient's body positioned therebetween, for receiving a portion of said radiation beam, said receiving means including an active array of detector elements for accumulating electrical charge indicative of said received portion of the radiation beam, said receiving means further including shifting means for incrementally shifting and reading out said accumulated electrical charge during each of a plurality of shifting intervals to form said composite image;

during receiving of said radiation signal scanning said receiving means by movement of the receiving means along a scanning path;

monitoring said scanning movement and producing at least one output, said output being responsive to velocity variations in the scanning movement; and processing said output so as to generate and vary a rate of shifting voltages for said shifting means wherein a substantially fixed relationship is maintained between the selected region being imaged and the position of the corresponding accumulated charge within the array during scanning, irrespective of variations in the velocity of said scanning movement, wherein durations corresponding with said shifting intervals are varied in response to said velocity variations.

10. The method of claim 9, said processing step further comprising the steps of:

generating said shifting voltages at a predetermined frequency; and modifying said predetermined frequency, based on said output, to compensate for any variations in said scanning movement.

11. The method of claim 10 wherein:

said elements of said array are configured in a plurality of rows each of which defines a width with respect to said path, and wherein said scanning step includes the step of moving said receiver through a plurality of incremental movements along said path, each of which incremental movements corresponds to said width; and, said processing step generates said shifting voltages so as to cooperatively shift said accumulated charge in a direction opposite said scanning direction during said plurality of shifting intervals such that said substantially fixed relationship is maintained.

12. The method of claim 11, said monitoring step further comprising the step of:

measuring a first duration of a first one of said incremental movements, said first duration thereafter being used as said output.

13. The method of claim 12, said processing step further comprising the step of:

setting the duration for one of said shifting intervals, which occurs during a second one of said incremental movements immediately following the first incremental movement, to a period corresponding to the measured duration of said first incremental movement.

14. The method of claim 12, wherein:

said monitoring step further comprises the step of measuring and outputting a second duration of a second one of said incremental movements; and said processing step further comprises the steps of (i) comparing the first duration with the second duration and (ii) setting one of said shifting intervals, which occurs during a third incremental movement, to said second duration, if the first duration is different than the second duration.

15. The method of claim 12, further comprising the step of:

mapping a plurality of expected scanning rates of the receiving means along said path, wherein said processing step determines a current location of said receiving means and, thereafter, generates said shifting voltages based on said output and said expected scanning rate at the current location of the receiver.

16. The method of claim 11, said monitoring step further comprising the steps of:

producing a series of pulses corresponding to a plurality of predetermined positions of said receiving means along said path such that, during scanning of the receiving means, a predetermined plurality of pulses is generated during each of said increment movements so that any change in the rate at which said pulses are produced is substantially attributable to a change in the scanning rate;

counting said predetermined number of pulses so as to establish the conclusion of one increment; and measuring said output as a period of time over which said predetermined number of pulses is counted.

17. An apparatus for use in generating a composite image of a selected region of a patient's body, said apparatus comprising:

source means for transmitting a radiation beam through said selected region of said patient's body;

receiving means, disposed in opposing relation to said source means with said selected region of said patient's body positioned therebetween, for receiving a portion of said radiation beam, said receiving means including an active array of detector elements for accumulating electrical charge indicative of said received portion of said radiation beam during scanning movement of the receiving means, said receiving means further including shifting means for at least one of incrementally shifting said accumulated electrical charge within said array and for reading out the accumulated charge therefrom during each of a plurality of shifting intervals;

scanning means for providing said scanning movement of said receiving means;

monitoring means for monitoring said scanning movement and for producing at least one output, said output being responsive to velocity variations in the scanning movement; and processing means for receiving said output and for providing a shifting signal to said shifting means so as to provide for at least one of incrementally shifting and reading out said charge during said plurality of shifting intervals for composing said composite image, said processing means being configured for modifying a rate of said shifting signal based, at least in part, on said output to account for said velocity variations wherein a substantially fixed relationship is maintained between the selected region being imaged and the position of the accumulated charge within the array during the scanning movement, and wherein durations corresponding with said shifting intervals are varied in response to said velocity variations.

18. An apparatus in accordance with claim 17 wherein:

the elements of said active array of detector elements are arranged in a plurality of rows and said shifting means transfers the accumulated charge from each row to an adjacent row during said shifting intervals.

19. An apparatus in accordance with claim 18, said processing means further comprising:

means for generating said shifting signal as a series of shifting pulses at a predetermined shifting frequency; and means for modifying said shifting frequency so as to control the duration of said shifting intervals.

20. The apparatus of claim 18 wherein:

each said row includes a width defined with respect to said scanning movement and wherein said receiving means moves a predetermined incremental distance during said scanning movement corresponding to the width of one row as the accumulated charge is shifted by one row in a direction that is opposite that of said scanning movement so as to maintain said substantially fixed relationship.

21. An apparatus in accordance with claim 20, said monitoring means further comprising:

encoder means for producing pulses at predetermined positions of said receiving means such that, during movement of the receiving means, a predetermined number of pulses is produced for each incremental movement at a pulse rate so that any change in said pulse rate is substantially attributable to a change in the rate of said scanning movement.

22. An apparatus in accordance with claim 21, said processing means further comprising:

means for counting said predetermined number of pulses so as to establish the completion of a first incremental movement of said receiver means; and means for measuring as said output a duration of said first incremental movement, after its completion, as the period over which said predetermined number of pulses was counted.

23. An apparatus in accordance with claim 21 wherein:

said encoder means generates at least 10 pulses per incremental movement.

24. An apparatus in accordance with claim 21, said encoder means further comprising:

an elongated encoder strip defining said predetermined positions, said encoder strip being fixedly attached within the apparatus so as to be stationary relative to said scanning movement; and reading means for reading said encoder strip during the scanning movement so as to generate said pulses during each said incremental movement.

25. An apparatus in accordance with claim 24, wherein:

said encoder strip and said reading means are cooperatively configured to produce one of said pulses for a scanning movement in which the receiving means moves a distance of approximately $60\mu \pm 0.5\%$ relative to the encoder strip.

26. An apparatus in accordance with claim 24, wherein:

said reading means moves in corresponding relationship with said receiving means while reading said encoder strip.

27. An apparatus in accordance with claim 18 wherein:

said scanning means includes means for moving said receiving means a predetermined incremental distance in relation to said selected region during each of said shifting intervals; and said monitoring means includes means for measuring and outputting a first duration for a first one of said incremental movements during a first one of said shifting intervals.

28. An apparatus in accordance with claim 27, said processing means further comprising:

means for modifying said shifting signal for a second shifting interval corresponding to a second one of said incremental movements, immediately following the first incremental movement, such that the duration of the second shifting interval is set to the measured duration of the first incremental movement.

29. An apparatus in accordance with claim 27 wherein:

said monitoring means further includes means for measuring and outputting a second duration for a second one of said incremental movements; and said processing means further includes means for comparing the first duration with the second duration and for setting a shifting interval, performed during a third incremental movement, to said second duration, if the first duration is different than the second duration.

30. An apparatus in accordance with claim 17, said processing means further comprising:

means for mapping an expected scanning rate of the receiving means at a plurality of incremental positions of the receiving means during the scanning movement and wherein said processing means includes means for determining a current location of said receiving means during a scan and, thereafter, modifies said shifting signal based on said output and said expected scanning rate at the current location of the receiver.

* * * * *